United States Patent
Lee et al.

(10) Patent No.: US 7,100,457 B2
(45) Date of Patent: Sep. 5, 2006

(54) METHOD FOR MEASURING RESIDUAL STRESS IN A SIAMESE REGION OF A CYLINDER BLOCK

(75) Inventors: Kyung Woo Lee, Seoul (KR); Chi Un Kim, Yongin (KR)

(73) Assignee: Hyundai Motor Company, Seoul (KR)

( * ) Notice: Subject to any disclaimer, the term of this patent is extended or adjusted under 35 U.S.C. 154(b) by 65 days.

(21) Appl. No.: 11/024,869

(22) Filed: Dec. 28, 2004

(65) Prior Publication Data
US 2005/0188772 A1    Sep. 1, 2005

(30) Foreign Application Priority Data
Feb. 26, 2004    (KR) ............... 10-2004-0013079

(51) Int. Cl.
*G01L 1/22*    (2006.01)

(52) U.S. Cl. ..................... 73/862.474; 73/115
(58) Field of Classification Search ........... 73/862.474
See application file for complete search history.

(56) References Cited
FOREIGN PATENT DOCUMENTS

JP          11-304603         11/1999
KR       1019990051769      7/1999

*Primary Examiner*—Edward Lefkowitz
*Assistant Examiner*—Lori Moorman
(74) *Attorney, Agent, or Firm*—Morgan Lewis & Bockius LLP

(57) ABSTRACT

Using a strain gauge attached at an interior side of a cylinder bore at a siamese region, a plurality of output values of the strain gauge can be detected during partially cutting the cylinder bore and residual stress of the siamese region can be calculated based on the plurality of the output values.

8 Claims, 4 Drawing Sheets ized cutting of the cylinder bore, and calculating residual stress of the siamese region based on the plurality of output values of the strain gauge.

METHOD FOR MEASURING RESIDUAL STRESS IN A SIAMESE REGION OF A CYLINDER BLOCK

CROSS-REFERENCE TO RELATED APPLICATION

This application claims priority to, and the benefit of, Korean Patent Application No. 10-2004-0013079 filed in the Korean Intellectual Property Office on Feb. 26, 2004, the entire content of which is incorporated herein by reference.

TECHNICAL FIELD OF THE INVENTION

Generally, the present invention relates to a method for measuring residual stress. More particularly, the method for measures residual stress of a siamese region of a cylinder block of an engine through partially cutting the siamese region.

BACKGROUND OF THE INVENTION

Many of the parts used for vehicles are produced by casting and are internally subject to residual stress. That is, such a part is very likely to experience high residual stress due to shrinkage after casting and high residual stress greatly shortens the fatigue life of the part.

Cylinder blocks of an engine are typically made of aluminum material for lightness and better fuel consumption of a vehicle. However, cast iron material is still applied to an interior of a cylinder bore to prevent deterioration of the rigidity and/or fatigue life of a cylinder block. Such a cast iron material and aluminum have different coefficients of thermal expansion. Therefore, relatively high residual stress is formed at a siamese region where adjacent cylinder bores meet on the top of the cylinder block after casting of the cylinder block.

Residual stress formed at the siamese region may cause a crack so as to deteriorate fatigue strength and durability of an engine. Consequently, measurement of residual stress of a siamese region of a cylinder block is required during development of a new engine. When the residual stress is measured to be higher than a standard, the manufacturing method or structure of the cylinder block should be changed so as to lower the residual stress.

Residual stress is typically measured by a cutting or non-cutting method. A non-cutting method does not cause damage to a fabricated article since a crystalline structure may be analyzed using X-ray, ultrasonic wave, electromagnetic wave, or etc. According to a cutting method, the degree of residual stress is measured by measuring deformation of the article that is produced by removal of residual stress due to cutting of the article.

Among various schemes for such a cutting method, a drilling scheme and a full cutting scheme are most widely used. According to the drilling scheme, strain gauges are respectively attached to 0°, 120°, and 270° positions around a target area of measurement, in a generally circular arrangement. Subsequently, deformation, and accordingly residual stress, of the article is measured by the strain gauges positioned therearound, while the target area is being removed by a drill or laser.

On the other hand, according to a full cutting scheme, a strain gauge is attached at a target area of the residual stress measurement. Then, the target area is fully separated from the article by cutting the article along a full circumference around the strain gauge. A resultant deformation, and equivalently residual stress, is then measured.

Each of the above mentioned conventional methods have associated drawbacks. A drawback of the non-cutting method is that a very expensive and complicated apparatus is required. In addition thereto, since a cylinder block of an engine is very big in size for such an apparatus, such a non-cutting method is not believed to be appropriate for a measurement of residual stress of a cylinder block. A drawback of the drilling scheme includes the fact that a relatively wide area around the target area of the measurement should be secured to be attached with strain gauges. However, a siamese region of a cylinder block does not provide sufficient neighboring area, and accordingly, it is not a good example for an application of such a drilling scheme.

Therefore, according to a conventional scheme for measuring residual stress of a siamese region of an engine, a full cutting scheme is widely adopted, and accordingly, a target area of measurement attached with a strain gauge is fully separated from the article by cutting the article along a full circumference around the strain gauge. However, according to such a full cutting scheme, measurement of residual stress requires excessive time, since a siamese region should be fully separated from a cylinder block.

The information disclosed in this Background of the Invention section is only for enhancement of understanding of the background of the invention and should not be taken as an acknowledgement or any form of suggestion that this information forms the prior art that is already known in this country to a person of ordinary skill in the art.

SUMMARY OF THE INVENTION

The present invention provides a method for measuring residual stress that does not necessitate full departing of a siamese region from an engine cylinder block. One embodiment of the method includes attaching a strain gauge at an interior side of a cylinder bore at the siamese region. Detecting a plurality of output values of the strain gauge during partially cutting the cylinder bore, and calculating residual stress of the siamese region based on the plurality of the output values of the strain gauge.

In a further embodiment, the detecting of a plurality of output values of the strain gauge detects consecutive output values of the strain gauge. The consecutive output values being detected during cutting the cylinder bore at both sides of the strain gauge in an axial direction from an end of the cylinder bore. Also, in this embodiment, the calculating of the residual stress may be realized by determining if a change rate of the consecutive output values of the strain gauge is below a predetermined rate and calculating the residual stress based on a last output value of the strain gauge in the case that the change rate of the consecutive output values of the strain gauge is below the predetermined rate. In a further embodiment, the predetermined change rate is from 0% to not more than about 2%.

According to another embodiment, a system for measuring residual stress of a siamese region of an engine cylinder block includes a strain gauge attached to the siamese region, a cutting device for cutting the siamese region attached with the strain gauge, and a controller for calculating the residual stress of the siamese region on the basis of output values of the strain gauge. The controller is preferably a microprocessor activated by a predetermined program. The controller is programmed to execute instructions for detecting a plurality of output values of the strain gauge during partially cutting the cylinder bore and calculating residual stress of the siamese region based on the plurality of output values of the strain gauge.

In a further embodiment, the detecting of a plurality of output values of the strain gauge detects consecutive output values of the strain gauge. The consecutive output values are detected during cutting the cylinder bore at both sides of the strain gauge in an axial direction from an end of the cylinder bore. Also, in this case, the calculating of the residual stress may be realized by determining if a change rate of the consecutive output values of the strain gauge is below a predetermined rate and calculating the residual stress based on a last output value of the strain gauge in the case that the change rate of the consecutive output values of the strain gauge is below the predetermined rate.

BRIEF DESCRIPTION OF THE DRAWINGS

The accompanying drawings illustrate exemplary embodiments of the present invention, and read, together with the description, serve to explain the principles of the present invention, wherein.

DETAILED DESCRIPTION OF THE EMBODIMENTS

Figure 1:
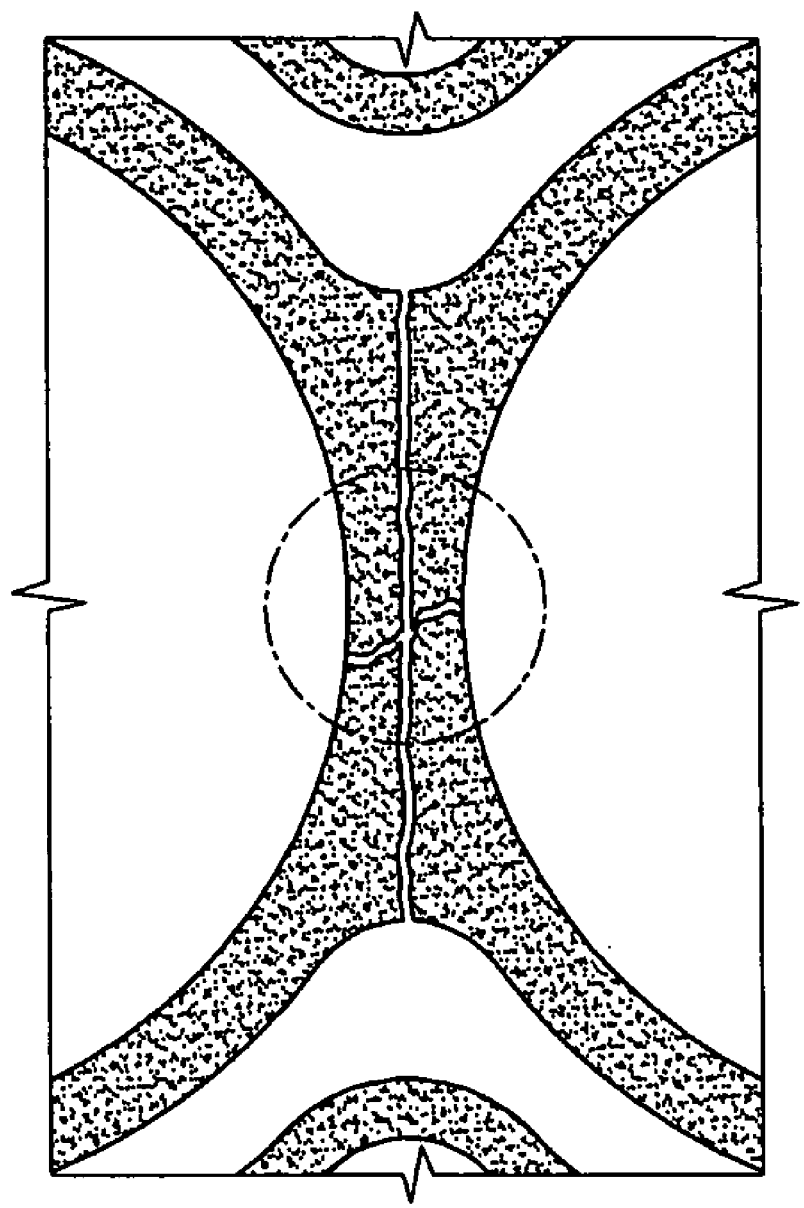
FIG. 1 illustrates a crack at a siamese region of a cylinder block caused by residual stress.
Figure 2:
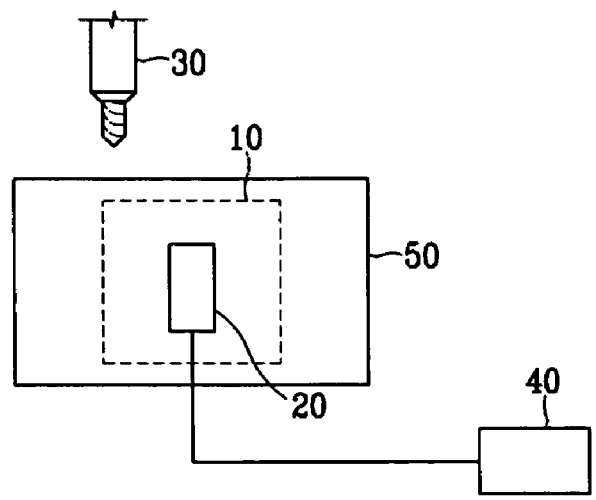
FIG. 2 is a block diagram of a system for realizing a method for measuring residual stress according to an embodiment of the present invention.
Figure 4:
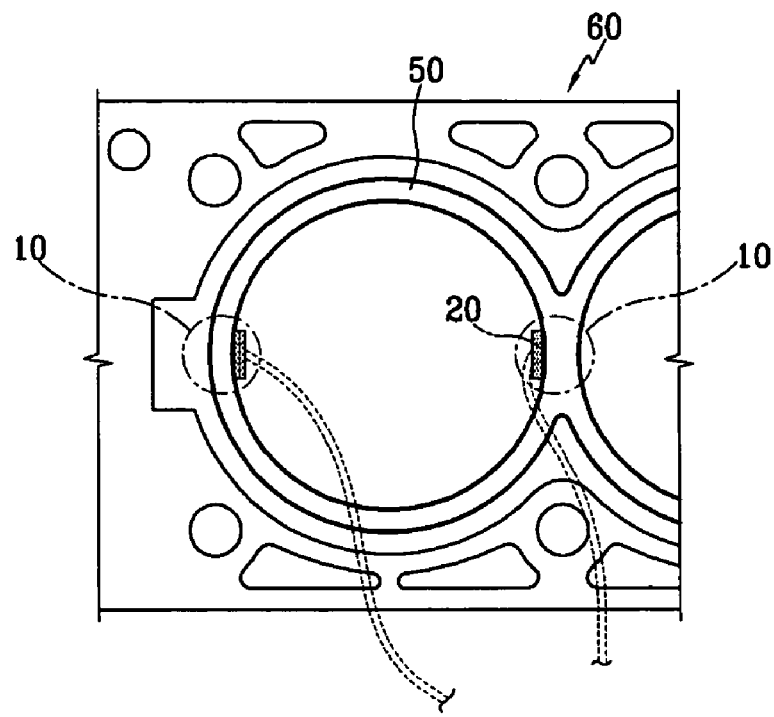
FIG. 4 illustrates a cylinder block attached with strain gauges according to a method for measuring residual stress according to an embodiment of the present invention.

According to FIG. 2, a system for realization of a method for measuring residual stress includes a strain gauge 20 attached to a siamese region 10 of a cylinder bore 50 of an engine cylinder block 60 (FIGS. 4 and 5), a cutting device 30 for cutting the siamese region 10, and a controller 40 for calculating the residual stress of the siamese region 10 on the basis of output values of the strain gauge 20. The strain gauge 20, attached to the siamese region 10, generally fixed to an interior circumference of the cylinder bore 50. A cylinder block 60 having a cylinder bore 50 attached with the strain gauge 20 is shown in FIG. 4.

The output terminal of the strain gauge 20 is connected to the controller 40, so that output values of the strain gauge 20 are delivered to the controller 40. The controller 40 is a microprocessor activated by a predetermined program and is programmed to calculate the residual stress of the siamese region 10 on the basis of output values (e.g., current values) of the strain gauge 20. The cutting device 30 may be a drill or an end mill used to cut the cylinder bore near the strain gauge 20.

Figure 3:
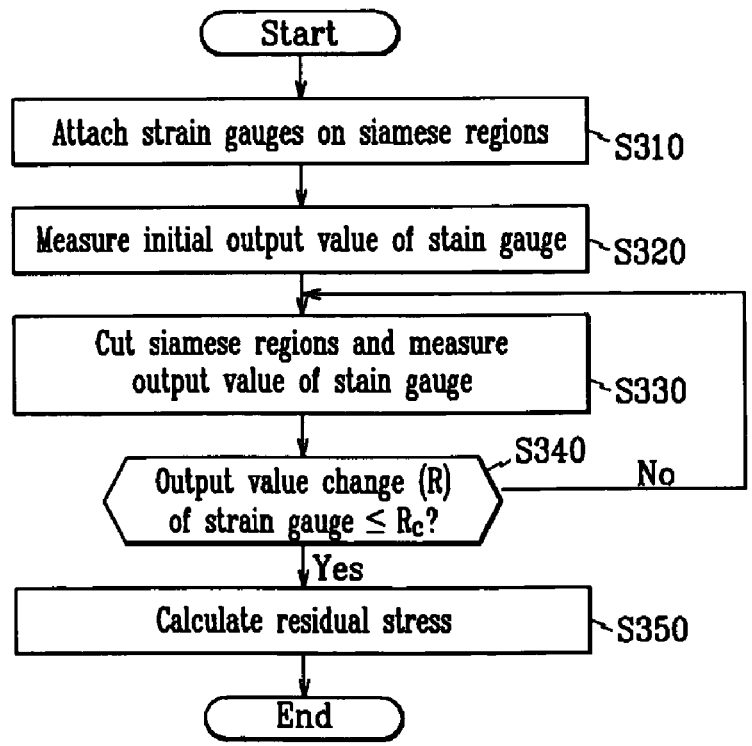
FIG. 3 is a flowchart for showing a method for measuring residual stress according to an embodiment of the present invention.

As shown in FIG. 3, the method of measuring residual stress includes, first, step S310, a strain gauge 20 is attached to an interior circumference of the cylinder bore 50 at the siamese region 10 where cylinder bores 50 of the engine cylinder block 60 are conjoined. The strain gauge 20 is also connected to the controller 40. Subsequently, step S320, the controller 40 detects and stores an initial value (e.g., initial current value) of the strain gauge 20 attached to the siamese region 10, before the siamese region 10 of engine cylinder block 60 is cut. Then, at step S330, the controller 40 detects consecutive output values of the strain gauge 20 produced during cutting the cylinder bore 50 at both sides of the strain gauge 20 in an axial direction from an end of the cylinder bore 50.

Figure 5:
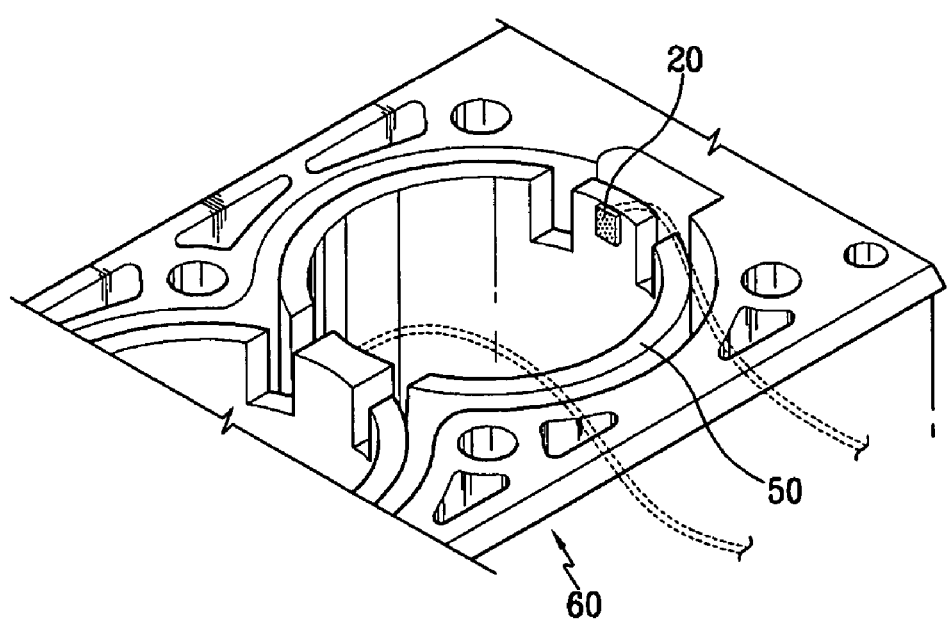
FIG. 5 illustrates a partial cutting of a siamese region according to a method for measuring residual stress according to an embodiment of the present invention.

FIG. 5 illustrates a partial cutting of the siamese region 10 cut by the cutting device 30. As shown in FIG. 5, the cutting direction of the siamese region 10 is an axial direction of the cylinder bore 50, and the siamese region 10 is cut at both sides of the strain gauge 20. In this case, the siamese region 10 is cut in a stepwise fashion. As a cut depth of the cylinder bore increases, the strain gauge 20 produces output values corresponding to the deformation of the siamese region 10 due to residual stress and transfers the output values to the controller 40.

Subsequently at step S340, the controller 40 calculates the change rate R of consecutive output values of the strain gauge 20 and then determines if the change rate R is smaller than or equal to a predetermined change rate $R_C$. When the change rate R of the output values is less than the predetermined change rate $R_C$, the controller 40 calculates the residual stress based on a last output value of the strain gauge 20, step S350. When the change rate R of the output values is found to be higher than the predetermined change rate $R_C$, the controller 40 returns to the step S330 such that the siamese region 10 is further cut by the cutting device 30 and then resultant output value of the strain gauge 20 may be detected again. That is, residual stress is repeatedly measured while the siamese region 10 is gradually cut at its both sides in the axial direction of the cylinder bore 50 as shown in FIG. 5.

Figure 6:
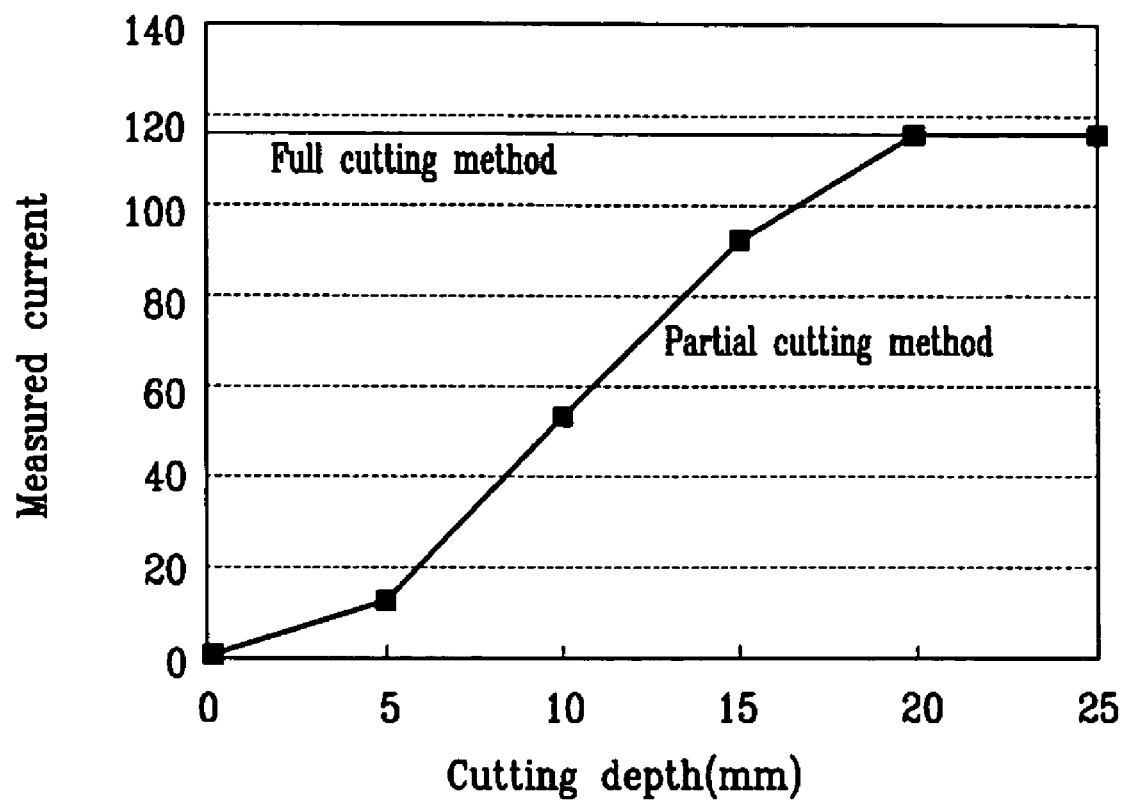
FIG. 6 is a graph showing comparison of output values obtained by a conventional full cutting scheme and a partial cutting scheme according to an embodiment of the present invention.

As shown in FIG. 6, output values of the strain gauge 20 of the present embodiment are compared with output values obtained by a conventional full cutting method. Output values of the strain gauge 20, according to an embodiment of the present invention, have a change rate that becomes less than a predetermined rate when the siamese region 10 is cut by more than a certain depth (e.g., 20 mm). This implies that, when the siamese region 10 is cut by sufficient depth, further cutting does not produce further deformation of the siamese region 10.

Calculation of residual stress from output values (e.g., current values) of the strain gauge 20 will be obvious to a person of ordinary skill in the art, and therefore, is not described in further detail.

While this invention has been described in connection with what is presently considered to be the most practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A method for measuring residual stress of a siamese region of an engine cylinder block using a strain gauge, the method comprising:

attaching a strain gauge at an interior side of a cylinder bore at the siamese region;

detecting a plurality of output values of the strain gauge during partially cutting the cylinder bore; and calculating residual stress of the siamese region based on the plurality of output values of the strain gauge.

2. The method of claim 1, wherein the detecting of a plurality of output values of the strain gauge detects consecutive output values of the strain gauge, the consecutive output values being detected during cutting the cylinder bore at both sides of the strain gauge in an axial direction from an end of the cylinder bore, and wherein the calculating of the residual stress comprises:
   determining if a change rate of the consecutive output values of the strain gauge is below a predetermined rate; and
   calculating the residual stress based on a last output value of the strain gauge in the case that the change rate of the consecutive output values of the strain gauge is below the predetermined rate.

3. The method of claim 2, wherein the predetermined change rate is between 0% and not more than about 2%.

4. A system for measuring residual stress of a siamese region of an engine cylinder block, the system comprising:
   a strain gauge attached to the siamese region;
   a cutting device for cutting the siamese region attached with the strain gauge; and
   a controller for calculating the residual stress of the siamese region on the basis of output values of the strain gauge, wherein the controller is a microprocessor activated by a predetermined program and is programmed to execute instructions for:
      detecting a plurality of output values of the strain gauge during partially cutting the cylinder bore; and
      calculating residual stress of the siamese region based on the plurality of output values of the strain gauge.

5. The system of claim 4, wherein the instructions for detecting a plurality of output values comprise instructions for detecting consecutive output values of the strain gauge, the consecutive output values being detected during cutting the cylinder bore at both sides of the strain gauge in an axial direction from an end of the cylinder bore, and wherein the instructions for calculating residual stress comprise instructions for:
   determining if a change rate of the consecutive output values of the strain gauge is below a predetermined rate; and
   calculating the residual stress based on a last output value of the strain gauge in the case that the change rate of the consecutive output values of the strain gauge is below the predetermined rate.

6. The system of claim 5, wherein the predetermined change rate is between 0% and not more than about 2%.

7. A method for measuring residual stress of a siamese region of an engine cylinder block, comprising:
   attaching a strain gauge at an interior side of a cylinder bore at a siamese region;
   detecting a plurality of output values of the strain gauge at predetermined cutting depths of the cylinder bore; and
   calculating residual stress of the siamese region based on the plurality of output values of the strain gauge.

8. The method of claim 7, wherein the calculating comprises:
   determining if a change rate of the consecutive output values of the strain gauge is below a predetermined rate; and
   calculating the residual stress based on a last output value of the strain gauge if the change rate of the consecutive output values of the strain gauge is below the predetermined rate.

* * * * *